(12) United States Patent
Harmsen et al.

(10) Patent No.: US 7,145,045 B2
(45) Date of Patent: Dec. 5, 2006

(54) PROCESS FOR THE PREPARATION OF ALKANEDIOL

(75) Inventors: Gerrit Jan Harmsen, Amsterdam (NL); Evert van der Heide, Amsterdam (NL); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 481 days.

(21) Appl. No.: 10/820,516

(22) Filed: Apr. 8, 2004

(65) Prior Publication Data

US 2004/0267058 A1 Dec. 30, 2004

(30) Foreign Application Priority Data

Apr. 9, 2003 (EP) .................... 03252261

(51) Int. Cl.
*C07C 27/00* (2006.01)
(52) U.S. Cl. .................................... 568/867
(58) Field of Classification Search .............. None
See application file for complete search history.

(56) References Cited

U.S. PATENT DOCUMENTS

| 4,400,559 A | 8/1983 | Bhise .................. 568/858 |
| 5,847,189 A | 12/1998 | Tojo et al. ............. 558/277 |
| 6,080,897 A | 6/2000 | Kawabe ................ 568/858 |
| 6,187,972 B1 | 2/2001 | Kawabe et al. ......... 568/858 |

FOREIGN PATENT DOCUMENTS

| EP | 125915 | 11/1984 |
| EP | 776890 | 6/1997 |
| GB | 2.098.985 | 12/1982 |
| WO | WO 99/45235 | 9/1999 |
| WO | 00/35840 | 6/2000 |
| WO | 03/042141 | 5/2003 |

OTHER PUBLICATIONS

International Search Report, dated Jul. 1, 2004.
International Preliminary Examination Report dated Aug. 18, 2005.

*Primary Examiner*—Sikarl A. Witherspoon

(57) ABSTRACT

The invention relates to a process for the preparation of alkanediol, which process involves (a) contacting alkylene oxide with carbon dioxide in the presence of catalyst to obtain a first liquid reaction mixture containing cyclic carbonate, (b) optionally removing carbon dioxide and/or alkylene oxide, (c) increasing the pressure of the liquid reaction mixture obtained in step (a) and/or (b), (d) contacting the pressurized first reaction mixture obtained in step (c) with water in the presence of catalyst to obtain a second reaction mixture containing alkanediol and carbon dioxide, (e) separating the second reaction mixture into a liquid effluent and a gaseous effluent containing carbon dioxide, and (f) recycling at least part of the gaseous effluent containing carbon dioxide to step (a), in which process the pressure in step (d) is higher than the pressure in step (a).

16 Claims, No Drawings

PROCESS FOR THE PREPARATION OF ALKANEDIOL

FIELD OF THE INVENTION

The present invention relates to a process for the preparation of alkanediol from alkylene oxide.

BACKGROUND OF THE INVENTION

Cyclic alkylene carbonates may be obtained by contacting alkylene oxide with carbon dioxide in the presence of a suitable catalyst. Such a process has been described, for example, in EP-A-119840. In addition, the cyclic alkylene carbonate may be further reacted. A conventional further process comprises hydrolysis of the cyclic alkylene carbonate to produce a diol as is described in U.S. Pat. No. 5,847,189.

U.S. Pat. No. 6,407,279 discloses the integration of the above steps such that cyclic carbonate may be fed to the transesterification reaction zone without purification of the cyclic carbonate. U.S. Pat. No. 6,407,279 also describes that the elimination of the cyclic carbonate purification step causes elimination of two vacuum distillation columns and gives a yield benefit by eliminating losses of cyclic carbonate attributable to the purification steps. The carbonation reaction of U.S. Pat. No. 6,407,279 is carried out at a pressure in the range from about 500 psia to about 1000 psia while the transesterification reaction is carried out at a pressure of about 100 psia to 300 psia.

SUMMARY OF THE INVENTION

The present invention is directed to a process for the preparation of alkanediol, which process comprises:
(a) contacting alkylene oxide with carbon dioxide in the presence of catalyst to obtain a first liquid reaction mixture containing cyclic carbonate,
(b) optionally removing carbon dioxide and/or alkylene oxide,
(c) increasing the pressure of the liquid reaction mixture obtained in step (a) and/or (b),
(d) contacting the pressurized first reaction mixture obtained in step (c) with water in the presence of catalyst to obtain a second reaction mixture containing alkanediol and carbon dioxide,
(e) separating the second reaction mixture into a liquid effluent and a gaseous effluent containing carbon dioxide, and
(f) recycling at least part of the gaseous effluent containing carbon dioxide to step (a),
in which process the pressure in step (d) is higher than the pressure in step (a).

DETAILED DESCRIPTION OF THE INVENTION

We have now found that an integrated process may be improved further. The improvement eliminates the need to increase the pressure of a gas or a mixture of gas and liquid.

Increasing the pressure of fluids may be done in many ways. The means employed usually is centrifugal force or transfer of momentum. In the chemical industry, centrifugal pumps or compressors are typically used, which are based on the principle of producing kinetic energy by the action of centrifugal force and then converting this energy into pressure by efficiently reducing the velocity of the flowing fluid. If transfer of momentum is used, one fluid is decelerated in order to transfer its momentum to a second fluid. Jets and eductors make use of transfer of momentum.

A common phenomenon in increasing the pressure of fluids is that increasing the pressure of a gas or a mixture of gas and liquid is more difficult than increasing the pressure of a liquid only. Apparatus for increasing the pressure of a gas or a mixture of gas and liquid have the disadvantage that they more easily fail in operation and are expensive.

The present invention makes it possible to operate while increasing the pressure of a liquid instead of having to increase the pressure of a gas or a mixture of gas and liquid.

In process step (a) of the present invention, the alkylene oxide is contacted with carbon dioxide in the presence of catalyst. Several catalysts are known to be suitable for such a process. Preferably, the catalyst is a homogeneous phosphorus containing catalyst. Phosphorus containing compounds which are suitable catalysts are phosphine compounds and phosphonium compounds. The catalyst preferably is a homogeneous phosphonium catalyst, more specifically a phosphonium halide catalyst. It was found especially advantageous to employ a tetraalkylphosphonium halide catalyst, more specifically a tributyl-methyl phosphonium iodide.

The catalyst may be either added as such or may be formed in-situ. The reaction mixture which is added to step (a), preferably is substantially free of water. The amount of water is preferably less than 5% wt, more preferably less than 1% wt, most preferably less than 0.1% wt, based on total amount of reaction mixture added.

The alkylene oxide for use in the present invention preferably is propylene oxide. The use of propylene oxide starting compound in the present invention, makes that propylene carbonate is formed in step (a) which leads to the manufacture of 1,2-propanediol or monopropylene glycol in step (b). In such process, the alkanediol is 1,2-propanediol and the alkylene oxide is propylene oxide.

The carbon dioxide may be either pure carbon dioxide or carbon dioxide containing further compounds. Carbon dioxide which is especially suitable for use in the present invention is carbon dioxide which has been separated off in subsequent steps of the present process. Carbon dioxide may either be separated off directly after the alkylene oxide has reacted with carbon dioxide or at a later stage.

Carbon dioxide is produced in the reaction of the cyclic alkylene carbonate with water. Therefore, it is especially attractive to separate carbon dioxide and recycle the carbon dioxide thus obtained to step (a) either as such or after having been purified. The extent to which the carbon dioxide is purified depends on the nature and the amounts of contaminants present in the carbon dioxide. These again depend on the exact reaction conditions and purification steps of the process.

Operating conditions for step (a) are known in the art. Preferred operating conditions will generally comprise a temperature of from 50° C. to 200° C., more specifically 100° C. to 150° C., and a pressure of at least $2 \times 10^5$ N/m$^2$, more specifically a pressure of from 2 to $100 \times 10^5$ N/m$^2$, most specifically of from 3 to $40 \times 10^5$ N/m$^2$. Preferably, process step (a) is carried out at a pressure of from 10 to $30 \times 10^5$ N/m$^2$.

The catalyst may be added to the reactor in any form known to be suitable to someone skilled in the art. Generally, the catalyst will be added as such or as a solution of the catalyst preferably in an inert solvent such as a cyclic carbonate or alkylene glycol. The catalyst may be added either to the alkylene oxide or to the carbon dioxide or to the mixture of both. Preferably, the catalyst solution is added to the reactor containing the mixture of alkylene oxide and carbon dioxide.

The reaction mixture obtained in step (a) is preferably used without further purification in the manufacture of alkanediol. However, some purification of the reaction mixture may be carried out. It may be advantageous to remove carbon dioxide and/or alkylene oxide from the first reaction mixture. The carbon dioxide and/or unconverted alkylene oxide which are separated off may be recycled to step (a). Separation of carbon dioxide and/or unconverted alkylene oxide may substantially reduce the volume of the reaction mixture to be subjected to steps (c) and (d). Additionally, the removal of carbon dioxide and/or unconverted alkylene oxide reduces the risk of cavitation in a pump.

In step (c), the pressure of the first reaction mixture obtained in step (a) and/or (b) is increased. The increase in pressure may be done in any way known to someone skilled in the art. Generally, a pump will be used which is known to be suitable for this specific application such as a centrifugal pump.

The pressurized liquid obtained in step (c) will generally have a pressure of from 1 to $100 \times 10^5$ N/m$^2$, more specifically of from 3 to $60 \times 10^5$ N/m$^2$, more specifically of from 5 to $50 \times 10^5$ N/m$^2$.

In a preferred embodiment, the feed subjected to step (d) contains a substantial amount of alkylene oxide. The presence of alkylene oxide may be due to the fact that part of the alkylene oxide has not been converted in step (a) and/or to the fact that alkylene oxide is added either before or during step (d). Preferably, the amount of alkylene oxide and cyclic carbonate in step (d) is such that the molar ratio of alkylene oxide to cyclic carbonate is from 0.01:1 to 1:1, more preferably from 0.02:1 to 0.6:1, more preferably from 0.03:1 to 0.4:1, more preferably from 0.04:1 to 0.3:1, more preferably from 0.05:1 to 0.2:1. Most preferably, the molar ratio of alkylene oxide to cyclic carbonate is from 0.08:1 to 0.15:1.

In the process according to the present invention, it is preferred that process step (a) is carried out with a homogeneous catalyst and step (d) is carried out with a heterogeneous catalyst. More preferably, the homogeneous catalyst present in step (a) is not removed until after step (d). This has the advantage that the homogeneous catalyst of step (a) may be active in the conversion of the alkylene oxide if alkylene oxide is still present in step (d). Removal of a limited amount of the homogeneous catalyst such as in distillation of part or all of the reaction mixture, will generally still leave sufficient homogeneous catalyst in the reaction mixture to serve its purpose in step (d) of the present process.

In step (d), at least part of the pressurized reaction mixture obtained in step (c) is hydrolyzed. Although it is possible to process only part of the product of step (c), generally, substantially all of the pressurized liquid obtained will be subjected to step (d).

In the present process, water is added in step (d) to the pressurized reaction mixture obtained in step (c). Although alcohol such as methanol may be added in addition to water, it is preferred to add water only. The presence of water only results in a more limited number of products, which is advantageous in the subsequent separation of products.

The catalysts for use in the present invention are known in the art. Preferably, the catalysts are heterogeneous catalysts. Examples of such catalysts comprise solid inorganic compounds such as alumina, silica-alumina, alumina carrying a copper compound, silica-alumina carrying a copper compound, silica-magnesia, aluminosilicate, gallium silicate, zeolites, metal-exchanged zeolites, ammonium-exchanged zeolites, zinc on a support, lanthanum on a support, a mixture of aluminium and magnesium (hydr)oxide and ion-exchange resins.

Preferably, the catalyst employed in step (d) is chosen from the group consisting of a mixture of aluminium and magnesium (hydr)oxide, zinc on a support, lanthanum on a support and alumina. These catalysts will be described hereinafter in more detail.

The mixture of aluminium and magnesium (hydr)oxide preferably has a magnesium to aluminium molar ratio in the range of from 3 to 50, more preferably of from 4 to 20. In the preparation of the catalyst, generally a so-called mixed magnesium/aluminium hydroxide is formed. However, under working conditions, mixed magnesium/aluminium oxides may be present. Our reference to a mixture of aluminium and magnesium (hydr)oxide covers both mixtures of aluminium and magnesium hydroxide and mixtures of aluminium and magnesium oxide and a combination of both mixtures. These mixtures were found to give the highest activity at a molar ratio of more than 3, preferably more than 4. A preferred range was found to be from 4 to 20, more specifically from 5 to 15, most specifically from 5 to 10. Preferred catalysts are described in International application No. PCT/EP02/12640.

In another preferred embodiment of the present invention, the catalyst comprises a lanthanum compound on a support. A preferred catalyst comprises at least 7% wt of lanthanum supported on a support. The lanthanum compound preferably is La$_2$O$_3$ or a precursor thereof. Under reaction conditions, this lanthanum compound may be temporarily and/or reversibly converted due to the reaction conditions into lanthanum hydroxide (La(OH)$_3$), lanthanum-oxyhydroxide (LaO(OH)) and/or corresponding alcoholate species such as (La(OR)$_3$ or LaO(OR)).

As a support for the lanthanum containing catalyst any suitable support may be used. The support preferably is substantially inert under the reaction conditions and is provided with sufficient mechanical strength. Potential supports comprise clay minerals, inorganic supports such as Al$_2$O$_3$, SiO$_2$, MgO, TiO$_2$, ZrO$_2$, ZnO and mixtures thereof. Other examples are a kaolinite, a hallosyte, a chrysotile, a montmorillonite, a beidellite, a hectorite, a sauconite, a muscovite, a phlogopite, a biotite, a hydrotalcite and talc. Particularly preferred are the inorganic supports selected from the group consisting of Al$_2$O$_3$, SiO$_2$, MgO, TiO$_2$, ZrO$_2$, ZnO and mixtures thereof.

The lanthanum containing catalyst preferably comprises at least 7% wt of lanthanum, more specifically in the range of from 7 to 40% wt of lanthanum based on total amount of catalyst. The lanthanum containing catalyst may be produced using any suitable method. A preferred method comprises impregnating a support with a lanthanum containing salt, and subsequently drying and calcining the impregnated support. After impregnation, the impregnated support may be dried and subsequently calcined. Calcination is generally carried out at a calcination temperature from between 120° C. to 700° C. The catalyst activity may be increased even further if the catalyst is calcined at a temperature in the range of from 350° C. to 600° C. Preferred catalysts are described in PCT patent application PCT/EP02/12638.

A further catalyst which is especially suitable for use in step (d) of the present invention is a zinc supported catalyst. The support preferably is selected from the group consisting of Al$_2$O$_3$, SiO$_2$, MgO, TiO$_2$, ZrO$_2$, Cr$_2$O$_3$, carbon and mixtures thereof. The zinc supported catalyst may be prepared by impregnation of silica, alumina or mixtures of aluminium and magnesium (hydr)oxide with a zinc nitrate solution. Preferably, the zinc supported catalysts comprise at least 15% wt of zinc on a support having a surface area of at least 20 $m^2/g$, more preferably at least 40 $m^2/g$. Preferred catalysts are described in the patent applications claiming priority of European patent application No. 02256347.2.

A further catalyst which is preferably used is a catalyst consisting of alumina. Preferably, the alumina is gamma-alumina.

Step (d) of the present process is preferably carried out at a temperature of from 50° C. to 300° C., preferably of from 80° C. to 250° C., more specifically of from 100° C. to 200° C. The pressure may vary widely, and preferably is at least $1\times10^5$ $N/m^2$, more specifically at least $2\times10^5$ $N/m^2$. The pressure generally will be at most $100\times10^5$ $N/m^2$, more specifically at most $70\times10^5$ $N/m^2$, most specifically at most $60\times10^5$ $N/m^2$. Preferably, the pressure in step (d) is of from 5 to $50\times10^5$ $N/m^2$, more specifically of from 15 to $35\times10^5$ $N/m^2$.

The pressure at which step (d) is operated is higher than the pressure at which step (a) is operated. Generally, the pressure in step (d) will be at least sufficient to compensate for any pressure drop in the process as a whole. Preferably, the pressure in step (d) will be at least $0.1\times10^5$ $N/m^2$ higher than the pressure in step (a), more specifically at least $1\times10^5$ $N/m^2$ higher, preferably at least $2\times10^5$ $N/m^2$ higher. The pressure in step (d) generally will be at most $50\times10^5$ $N/m^2$ higher than the pressure in step (a), more specifically at most $20\times10^5$ $N/m^2$, more specifically at most $15\times10^5$ $N/m^2$, most specifically at most $10\times10^5$ $N/m^2$.

In step (e), the second reaction mixture is separated into a liquid effluent and a gaseous effluent containing carbon dioxide. Such separation may be carried out by sending the second reaction mixture to an empty vessel. The reaction mixture separates into a carbon dioxide rich gaseous phase and a liquid phase. The gaseous effluent containing carbon dioxide obtained in step (e) preferably is recycled directly to step (a), optionally after having been combined with fresh carbon dioxide. A direct recycle is considered to be a recycle in which no further compounds are separated off. However, the gas which is recycled directly may have been subjected to treatments causing a change in temperature and/or pressure such as heat exchange with one or more other streams either of the present process or of a different process.

The liquid effluent obtained in step (e) may be separated further. Preferably, the separation comprises (g) separating the liquid effluent obtained in step (e) further into a gaseous effluent rich in carbon dioxide and a liquid effluent, (h) contacting with water the gaseous effluent rich in carbon dioxide obtained in step (g), and (i) sending the water used in step (h) to step (d). The separation of step (g) preferably is carried out at a pressure of from 0.1 to $20\times10^5$ $N/m^2$, more specifically of from 1 to $15\times10^5$ $N/m^2$, most specifically of from 1 to $2\times10^5$ $N/m^2$. Alkanediol may be separated from the liquid effluent obtained in step (g).

In step (f), at least part of the gaseous effluent containing carbon dioxide is recycled to step (a). The carbon dioxide may be recycled to step (a) without the need to increase its pressure. Advantageously, the process according to the present invention may be carried out without increasing the pressure of any of the streams present in step (a) to (f) besides the increase in pressure attained in step (c).

Preferably, alkanediol is separated from the second reaction mixture. The alkanediol may be separated from the reaction mixture obtained in step (d), (e) and/or (g) in any way known in the art. A preferred separation comprises distillation of the second reaction mixture, preferably by vacuum distillation, optionally followed by further distillation of one or more of the distillate fractions and/or bottom fractions. One or more of the fractions separated will have a high content of alkylene glycol. Alkylene glycol obtained by distillation will usually be sufficiently pure to use as such. If required, small amounts of by-products may be removed separately.

We claim:

1. A process for the preparation of an alkanediol, which process comprises:
    (a) contacting an alkylene oxide with carbon dioxide in the presence of a catalyst to obtain a first liquid reaction mixture containing a cyclic carbonate;
    (b) optionally removing carbon dioxide and/or alkylene oxide;
    (c) increasing the pressure of the liquid reaction mixture obtained in step (a) and/or (b);
    (d) contacting the pressurized first reaction mixture obtained in step (c) with water in the presence of catalyst to obtain a second reaction mixture containing alkanediol and carbon dioxide;
    (e) separating the second reaction mixture into a liquid effluent and a gaseous effluent containing carbon dioxide; and,
    (f) recycling at least part of the gaseous effluent containing carbon dioxide to step (a),
    in which process the pressure in step (d) is higher than the pressure in step (a).

2. The process of claim 1, wherein step (d) is carried out at a pressure of from 5 to $50\times10^5$ $N/m^2$.

3. The process of claim 2, wherein step (a) is carried out at a pressure of from 3 to $40\times10^5$ $N/m^2$.

4. The process of claim 2, wherein the pressure in step (d) is at least $0.1\times10^5$ $N/m^2$ higher than the pressure in step (a).

5. The process of claim 2, wherein step (a) is carried out with a homogeneous catalyst and step (d) is carried out with a heterogeneous catalyst.

6. The process of claim 2, wherein the gaseous effluent obtained in step (e) is recycled directly to step (a), optionally after having been combined with fresh carbon dioxide.

7. The process of claim 2, which process further comprises separating alkanediol from the second reaction mixture.

8. The process of claim 2, which process further comprises:
    (g) separating the liquid effluent obtained in step (e) further into a gaseous effluent rich in carbon dioxide and a liquid effluent;
    (h) contacting with water the gaseous effluent rich in carbon dioxide obtained in step (g); and,
    (i) sending the water used in step (h) to step (d).

9. The process of claim 8, which process further comprises separating alkanediol from the liquid effluent obtained in step (g).

10. The process of claim 1, wherein step (a) is carried out at a pressure of from 3 to $40\times10^5$ $N/m^2$.

11. The process of claim 1, wherein the pressure in step (d) is at least $0.1\times10^5$ $N/m^2$ higher than the pressure in step (a).

12. The process of claim 1, wherein step (a) is carried out with a homogeneous catalyst and step (d) is carried out with a heterogeneous catalyst.

13. The process of claim 1, wherein the gaseous effluent obtained in step (e) is recycled directly to step (a), optionally after having been combined with fresh carbon dioxide.

14. The process of claim 1, which process further comprises separating alkanediol from the second reaction mixture.

15. The process of claim 1, which process further comprises:
a. separating the liquid effluent obtained in step (e) further into a gaseous effluent rich in carbon dioxide and a liquid effluent;
b. contacting with water the gaseous effluent rich in carbon dioxide obtained in step (g); and,
c. sending the water used in step (h) to step (d).

16. The process of claim 15, which process further comprises separating alkanediol from the liquid effluent obtained in step (g).

* * * * *